US005782891A

United States Patent [19]

Hassler et al.

[11] Patent Number: 5,782,891
[45] Date of Patent: Jul. 21, 1998

[54] IMPLANTABLE CERAMIC ENCLOSURE FOR PACING, NEUROLOGICAL, AND OTHER MEDICAL APPLICATIONS IN THE HUMAN BODY

[75] Inventors: Beth Anne Hassler, Crystal; Adriannus P. Donders, Andover; Craig L. Wiklund, Bloomington; Daniel A. Lyons, Arden Hills, all of Minn.

[73] Assignee: Medtronic, Inc., Minneapolis, Minn.

[21] Appl. No.: 632,730

[22] Filed: Apr. 15, 1996

Related U.S. Application Data

[63] Continuation-in-part of Ser. No. 260,639, Jun. 16, 1994, abandoned.

[51] Int. Cl.[6] .................................................... A61N 1/375
[52] U.S. Cl. ............................................................ 607/36
[58] Field of Search ........................................ 607/36, 37

[56] References Cited

U.S. PATENT DOCUMENTS

| | | |
|---|---|---|
| 3,177,406 | 4/1965 | Bernstein . |
| 3,334,275 | 8/1967 | Mandeville . |
| 4,006,748 | 2/1977 | Schulman . |
| 4,288,841 | 9/1981 | Gogal . |
| 4,614,194 | 9/1986 | Jones . |
| 4,616,655 | 10/1986 | Weinberg . |
| 4,740,414 | 4/1988 | Shaheen . |
| 4,785,827 | 11/1988 | Fischer . |
| 4,871,583 | 10/1989 | Monnier . |
| 4,991,582 | 2/1991 | Byers . |
| 5,030,796 | 7/1991 | Swanson . |
| 5,105,811 | 4/1992 | Kuzma . |
| 5,293,069 | 3/1994 | Kato . |
| 5,358,514 | 10/1994 | Schulman . |
| 5,406,025 | 4/1995 | Carlstedt . |
| 5,439,732 | 8/1995 | Nagasaka . |
| 5,440,805 | 8/1995 | Daigle . |
| 5,442,145 | 8/1995 | Imai . |
| 5,450,090 | 9/1995 | Gels . |
| 5,456,004 | 10/1995 | Swamy . |
| 5,478,972 | 12/1995 | Mizutani . |

FOREIGN PATENT DOCUMENTS 0331959  9/1989  European Pat. Off. .

OTHER PUBLICATIONS

Hassler, Beth Anne "Fast Turnaround Multilayer Corfired Ceramic Motherboard Fabrication" presented at ASM's 2nd Electronic Packaging: Materials and Processes Conference. Bloomington. MN Oct., 1985.
Strojnik et al.. "Pulsar™–Clarion™ Cochlear Stimulator Modified for Fees Application". pp. 27–29.
Meadows et al.. "Multichannel Implantable Electrical Stimulation System for Gait Assist and Exercise in the Stroke and Sci Population". pp. 38–41.

*Primary Examiner*—Scott M. Getzow
*Attorney, Agent, or Firm*—Harold R. Patton; Michael B. Atlass

[57] ABSTRACT

An implantable medical device with a ceramic enclosure has a novel multi-layered ceramic feedthrough substrate in place of a prior art glass-to-metal feedthrough substrate, leading to lower costs and a higher feedthrough density. Use in a metal enclosure is also disclosed.

21 Claims, 9 Drawing Sheets

5,782,891

IMPLANTABLE CERAMIC ENCLOSURE FOR PACING, NEUROLOGICAL, AND OTHER MEDICAL APPLICATIONS IN THE HUMAN BODY

This application is a continuation in part of Ser. No. 08/260,639, filed Jun. 16, 1994, now abandoned.

FIELD OF THE INVENTION

The present invention relates to the packaging of implantable medical devices such as artificial cardiac pacemakers and the like.

BACKGROUND OF THE INVENTION

Generally speaking, a cardiac pacemaker or implantable pulse generator (IPG) is an electrical device used to supplant some or all of an abnormal heart's natural pacing function, by delivering appropriately timed electrical stimulation signals designed to cause the myocardium of the heart to contract or "beat".

Using telemetry, modern pacemakers are often programmable with regard to data and functionality prior to, and even after implant. Typical pacemakers are enclosed by metal casings such as titanium, which has good body compatibility. However, metal enclosures often cause interference during telemetry.

To create pacemakers and other implantable medical devices with enclosures which are transparent to radio frequency (RF) waves during telemetry, the enclosure can be constructed of ceramic material, for example. Such is the approach of U.S. Pat. No. 4,785,827 issued to Fischer, and U.S. Pat. No. 4,991,582 issued to Byers et al. Both references are hereby expressly incorporated by reference.

The cost of building feedthroughs for implantable medical devices is not inexpensive. A single flexible wire feedthrough is high without including the cost of welding it into a titanium can. Efficient bulk process such as punching vias into boards and, screening to place conductors ought to be substitutable for tedious labor intensive assembly processes and expensive parts now used to produce feedthroughs. Likewise, the present inability to have a large number of closely spaced feedthrough conductors fixed in a single part makes it difficult to weld connections to the present feedthrough which are often loose or at least not exactly positioned pins. Problems with insulators and machining failures abound. Solder traces and pads for bonding ought to be usable in low-cost surface mount construction of medical devices, but because of the flexible wire feedthroughs currently in use this has not happened. Because of the sensitivity of implantable device circuits most have a capacitor linked to the connector block to protect them from EMI. Currently, expensive custom made disk shape capacitors are used or labor intensive means of fastening rectangular chip capacitors to the sides of feedthroughs are used for this purpose. Resistance spot welding or soldering the flexible feedthrough wires to brazed pins or blocks on the hybrid are now commonly used for connecting between the external connector of the feedthrough and the internal components in an implanted medical device. All these features of modern implantable device production generally result in high scrap costs and require labor intensive processes.

SUMMARY OF THE INVENTION

In view of the foregoing, it is a first object of the present invention to provide an implantable medical device which is nearly transparent to radio frequency waves for telemetering purposes.

It is a second object of the present invention to provide an implantable medical device wherein its feedthrough substrate provides for a higher density of feedthroughs.

It is a third object of the present invention to provide an implantable medical device wherein its feedthrough substrate is less expensive than prior art feedthrough substrates.

It is a fourth object of the present invention to provide an implantable medical device satisfying the above objects wherein its enclosure is ceramic.

It is a further object of the present invention to provide an implantable medical device wherein the feedthrough substrate is a ceramic multilayer element suitable for mounting within a metal shield of said implantable medical device.

It is a further object to connect via a ceramic multilayer feedthrough the inside circuits of a ceramic shelled implantable device and electrical elements outside said shell. Ceramic feedthroughs in accord with this invention may be substantially thinner and of smaller diameter than previous designs.

In order to satisfy the above objects and others, the present invention provides a packaging arrangement for the outer packaging of an implantable medical device at least including:

a ceramic enclosure having an opening for receiving circuitry of the implantable medical device; and a multilayered feedthrough substrate for coupling to the ceramic enclosure at edges around the opening, the substrate having multiple feedthroughs for electrically coupling the circuitry inside the enclosure to the outside of the enclosure.

Alternatively the invention may provide a ceramic feedthrough for a metallic or other biocompatible enclosure. Alternatively the invention may provide a feedthrough that is continuous with a ceramic enclosure.

The details of the present invention will be revealed in the following description with reference to the drawing.

BRIEF DESCRIPTION OF THE DRAWINGS

FIG. 5 is sectioned side view of a prior art wire feed through.

DETAILED DESCRIPTION OF THE INVENTION

Figure 1:
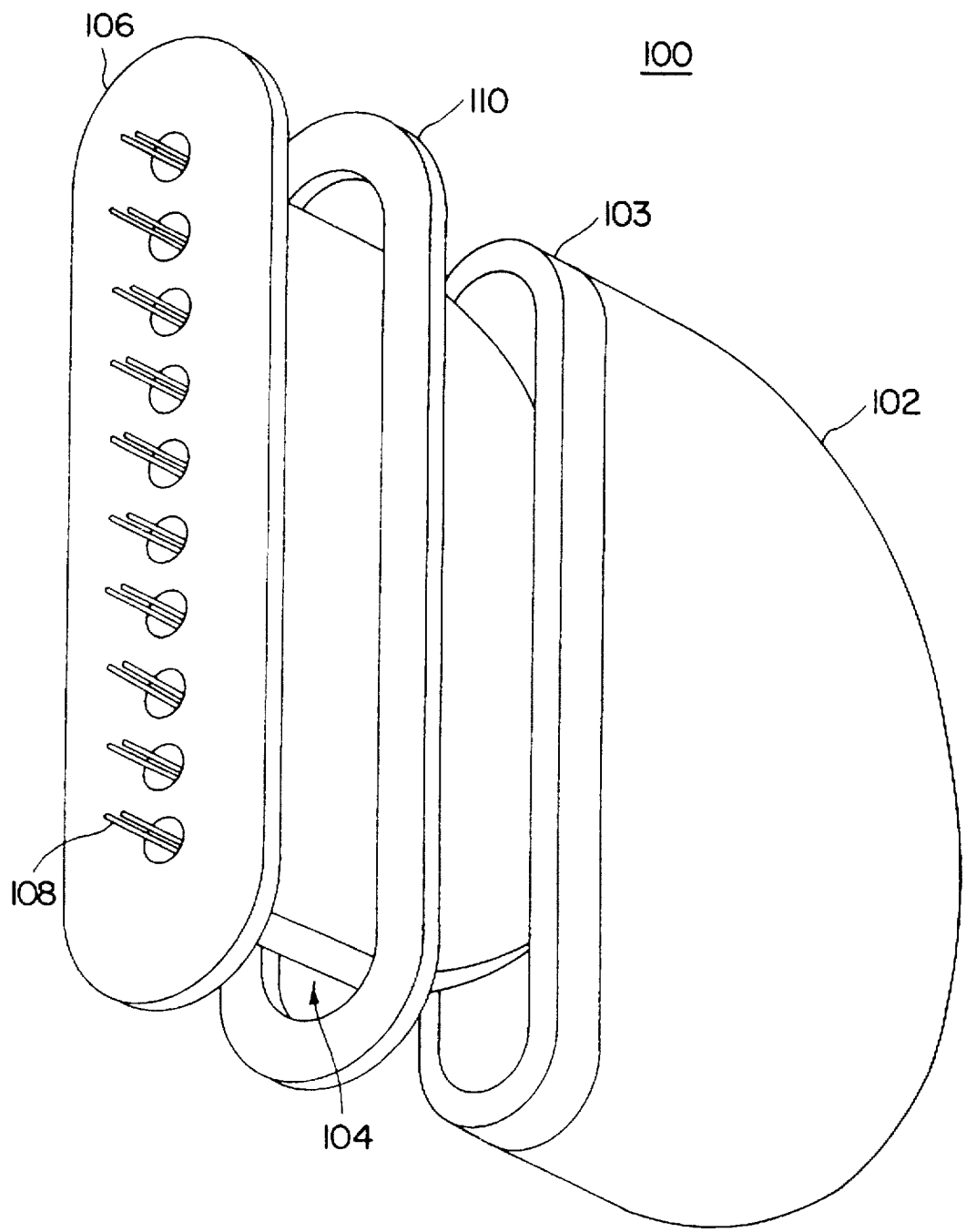
FIG. 1 is an exploded isometric view of a prior art pacemaker with a ceramic enclosure.

FIG. 1 shows a prior art packaging arrangement/scheme 100 for a pacemaker. The arrangement 100 has a ceramic enclosure 102 with a metalized portion 103. A hybrid circuit 104 is attached to a feedthrough substrate 106 which is a glass-to-metal feedthrough assembly. Feedthroughs 108 (metal) electrically connect to components of the hybrid circuit 104 at one end, and are adapted to electrically connect a connector block (not shown) at the other (exposed) end. A weld ring 110 is welded on one side to the enclosure 102 (at the metalized portion 103), and on its other side to the glass-to-metal feedthrough 106. The entire packaging provides an implantable medical device which is hermetically sealed.

Figure 2:
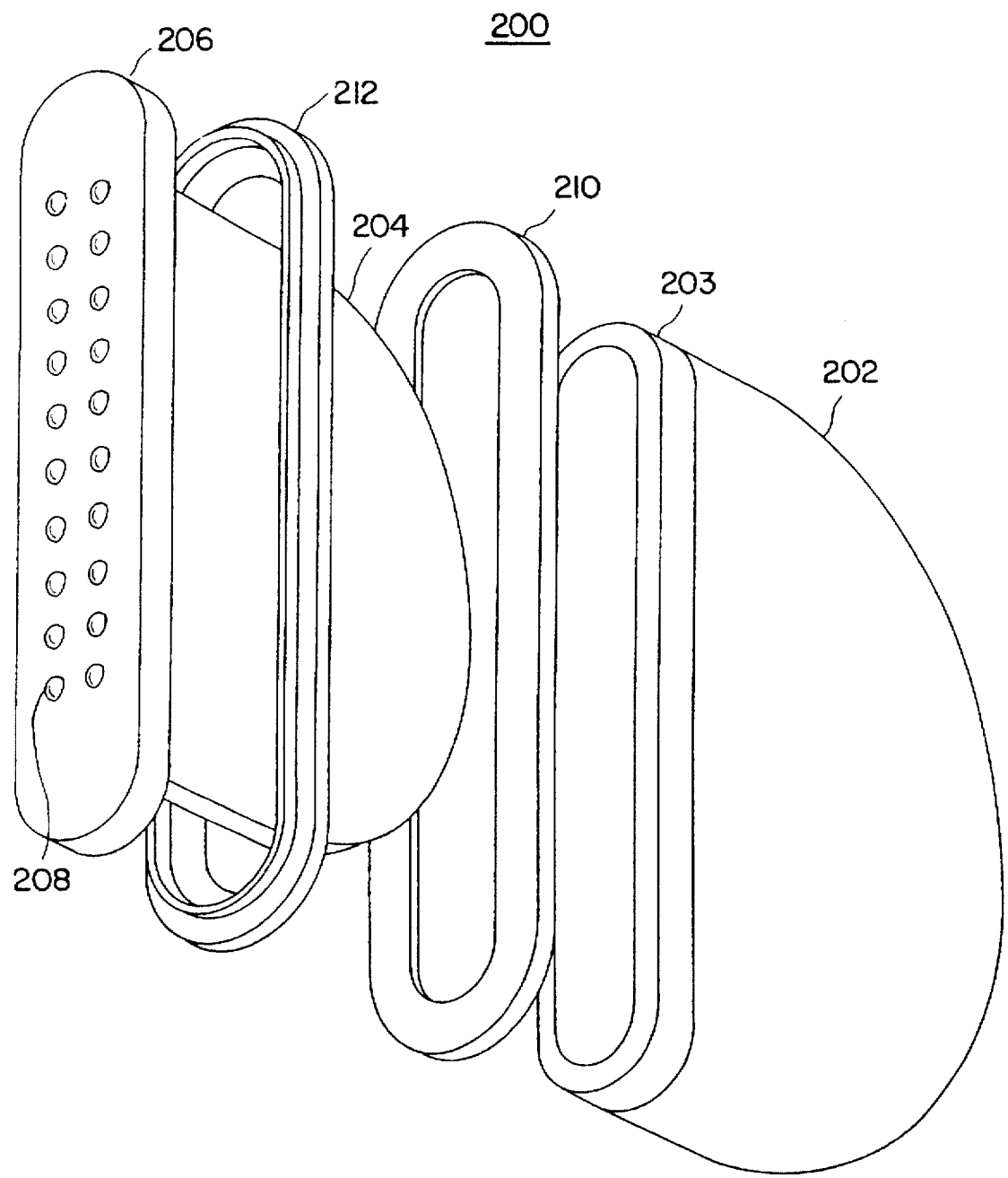
FIG. 2 is an exploded isometric view of a pacemaker employing the present-inventive features.

The present-inventive implantable medical device packaging arrangement/scheme 200 is illustrated in FIG. 2. The ceramic enclosure 202 is composed of biocompatible 99.5 percent aluminum oxide in the preferred embodiment, which has been shown to have good tissue compatibility. A metalized portion 203 is formed by sputtering (as is known in the art) a thin film of niobium on the ceramic surface.

A hybrid circuit 204 is connected to a novel multi-layered feedthrough substrate 206. The substrate 206 is composed of several layers of ceramic material with metal-plated input/output vias used to electrically connect the various layers. The plating metals may be gold and nickel, for example. As a result of the multi-layer and via configuration, a higher density of feedthroughs 208 are possible over the glass-to-metal feedthrough substrate (element 106 in FIG. 1) approaches in the prior art. The substrate 206 can be constructed using techniques known in the art, such as is disclosed by Beth A. Hassler in "Fast Turnaround Multilayer Cofired Ceramic Motherboard Fabrication," *Proceedings of ASM's 2nd Electronic Packaging: Materials and Processes Conference* (October 1985): 117–121. The above-mentioned article is hereby incorporated by reference.

Two weld rings 210 and 212 are chosen to have thermal expansion characteristics sufficiently similar to the ceramic material used to maintain good bonding over a broad temperature range. Weld ring 210 is brazed to the metalized portion 203 of the ceramic enclosure 202, and welded to the weld ring 212. Weld ring 212 is also brazed to the multi-layered feedthrough 206. The welded and brazed surfaces complete a hermetic seal of the pacemaker.

Figure 3:
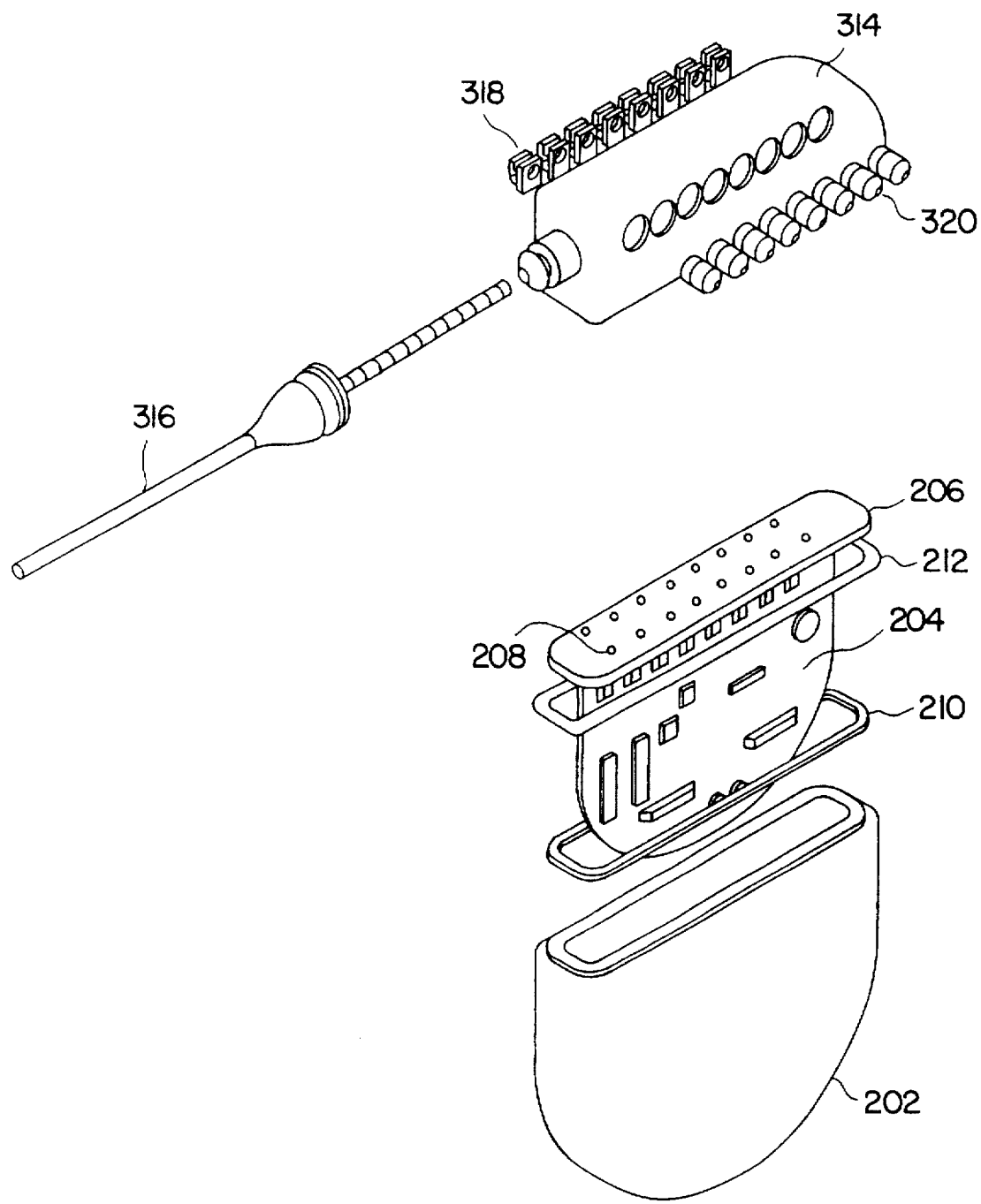
FIG. 3 is an exploded isometric view of the pacemaker in FIG. 2, additionally showing a connector block and a pacemaker lead.

FIG. 3 shows the pacemaker in FIG. 2 with additional components. Namely, the pacemaker also has a connector block 314 which is fastened to the multi-layered feedthrough substrate 206. The connector block 314 electrically connects one or more pacemaker leads 316 to the feedthroughs 208 via lead clamps 318. The lead 316 is firmly held in place (in the lead clamps 318) by tightening set screws 320.

Thus, electrical connection is made from the lead 316 to the connector block 314 to the feedthroughs 208 to the hybrid circuitry 204.

Variations and modifications to the present invention are possible given the above disclosure. However, such variations and modifications are intended to be within the scope of the invention claimed by this patent. For example, the packaging arrangement described supra, is optimal for bipolar pacing. The ceramic enclosure 202 may be partially or completely coated with a thin metal layer (using sputtering techniques, for example) to enable unipolar pacing.

Further Embodiments

The application of cofired ceramic multilayer feedthrough and other multilayer technologies for the implantable device field allows for numerous economically advantageous improvements over prior art devices.

Figure 4:
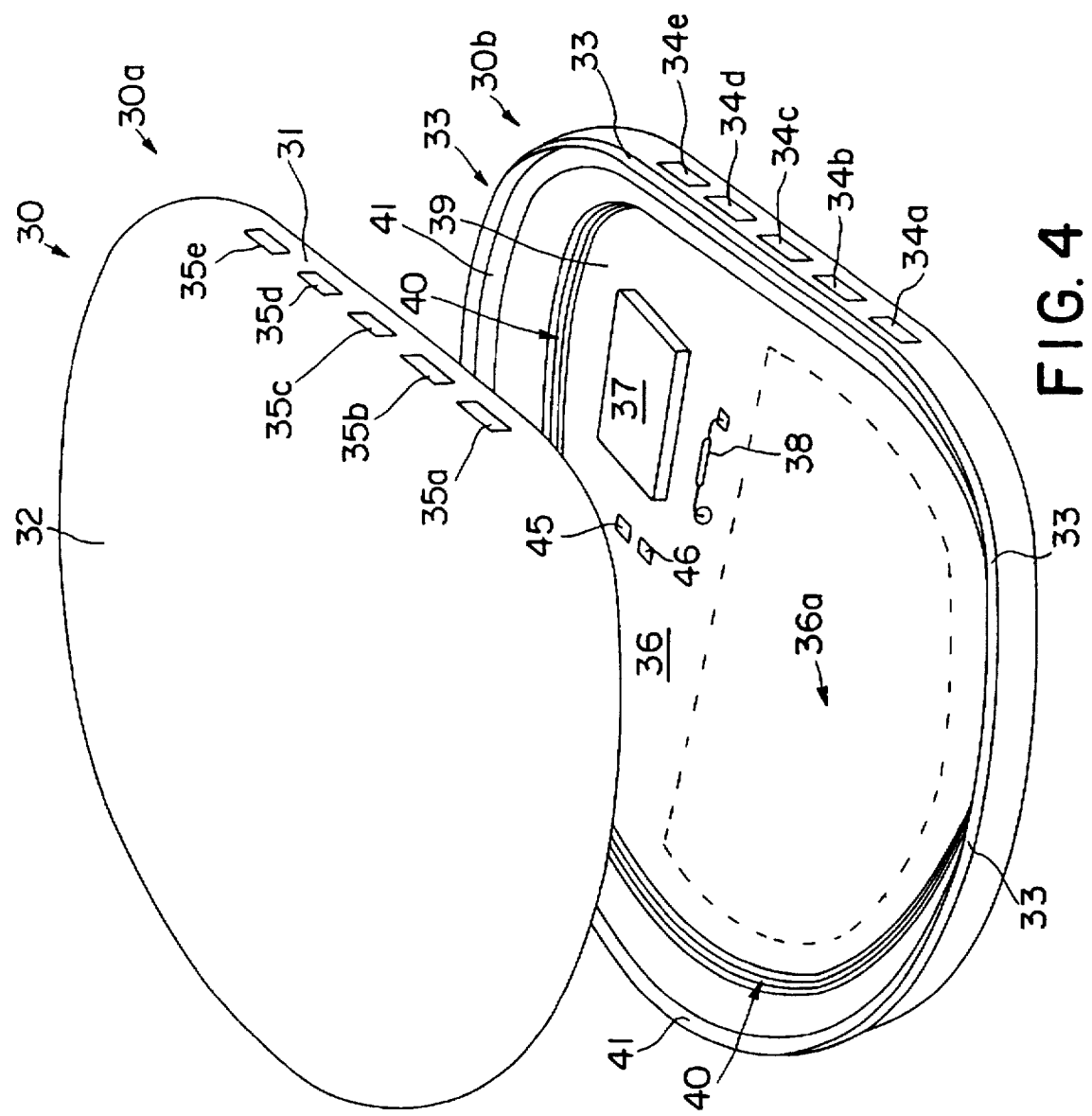
FIG. 4 is an exploded isometric view of a pacemaker housing such as could be manufactured in accord with a preferred embodiment of this invention in co-fired ceramic.

A heuristic model of a preferred embodiment application for this invention is illustrated in reference to FIG. 4 wherein an exploded view of a device 30 having two shell halves 30a and 30b, an exterior surface 32 and interior surface 36 and is used here for illustration purposes only, not to limit the invention's scope. A cofired ceramic multilayer board whose edge can be seen at 41 is molded into this shape (30a and 30b). A lip 33 formed of one or more of these ceramic layers protrudes above the surface of the edge of the board to provide for better mating with half 30a. By brazing, this lip can hold together halves or pieces of a ceramic device shell. Alternatively, lip 33 may be a metal strip for brazing or welding the two parts 30a and 30b together, where one of the two parts is a biocompatible metal such as titanium for example. The brazing surface could be flat rather than a raised ring if desired. Other joining techniques may be used as circumstances warrant, such as ceramic adhesives to join the two shell parts together.

In the preferred embodiments the ceramic is formed from sheets of 99.8% $Al_2O_3$ which are formed or held in a moldable polymer. Such polymeric ceramics can be made in accord with process described in U.S. Pat. Nos. 5,268,415 and 5,438,089, if preferred, or less moldable ceramics may be used for flat structures if desired. This concentration of $Al_2O_3$ can vary too, especially for those parts that are only used for feedthroughs (rather than for the shell or the hybrid circuit board because such parts will not be exposed to the body fluids into which the device would be implanted), but it is preferred. Where biocompatibility is not an issue for these materials (say if using for only a protected feedthrough) much less than 99.8% $Al_2O_3$ may be used. Beryllium oxide $ZrO_2$ or even low temperature co-fired ceramics may also be used because the feedthrough may be encapsulated and protected from the body. We prefer to co-fire layers laminated together to form conductive pathways between or through layers using tungsten metal which does not develop shrink mismatch at 1520° C.–1625° C., our preferred firing temperatures. The tungsten (also called Wolfram) metal can be thick film screen printed to form traces on the individual sheets of ceramic before firing. This is now done using a metal paste on the surface of stainless steel mesh forms. The preferred method for forming vias is to punch holes and extrude a tungsten paste through the vias. Although not preferred, resin films have been used in other industrial applications for multilayer connections as in U.S. Pat. No. 5,478,972 (Mizutani et al.) For most applications discussed here such resin film applications will not work.

Advantageously, this design provides for at least a plurality of external bonding pads such as bonding pads 34a–e and 35a–e. These may be laid out in a linear pattern which provides for cheap and easy assembly to wire bonding or flat cable matching assembly. Each such pad is preferably coated by plating, sputter coating, screening, brazing or welding with a precious metal or other surface preferably to facilitate wire-bonding or brazing or welding thereto. Each pad connects electrically with another pad in the interior, on the exterior or to an electrical element in the ceramic multilayer package, or an electrical component on the package.

To make for mounting a connector block the surface 31 into which these bonding pads are laid may be any shape desired. Here it is illustrated as flat because that is preferred for our applications.

In this particular embodiment 30, an antenna wire 40 is wound around the interior surface 36 of device half 30b. Antenna windings in or on or even within shells formed of ceramic multilayer parts are particularly advantageous in that they do not suffer from the severely attenuating RF losses inherent in transmitting through a titanium can as it is now the practice for construction of device shells for implanted devices. With no additional hybrid boards required, surface mount and other components 37, 38, respectively, may be mounted directly to an interior surface such as surface 36 through areas such as bonding pads 45 and 46 here shown unused in surface 36.

Figure 5:
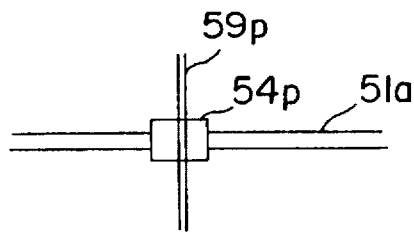
Figure 5A:
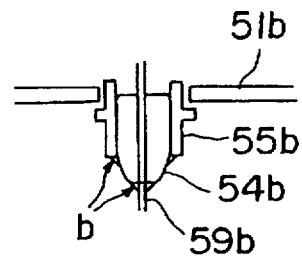
FIG. 5a is another section of sideview of another prior art feedthrough.

To facilitate an understanding of the advantages of this invention, attention is drawn to prior art FIGS. 5 and 5a. In FIG. 5a the surface of a glass bead 54p is melted into a metal surface 51a through which a flexible wire 59p is mounted. Such connections are in common use for non medical applications. In the medical field devices such as is shown in FIG. 5a are more likely. Commonly a connection is made like that of FIG. 5a where rather than melting the glass between the metal shells, a ceramic plug 54b is brazed into a metal (titanium) ferrule 55b that is later welded to the metal (usually titanium) shell or can 51b. Production costs for such feedthroughs are substantially greater per feedthrough than for this invention.

Figure 6:
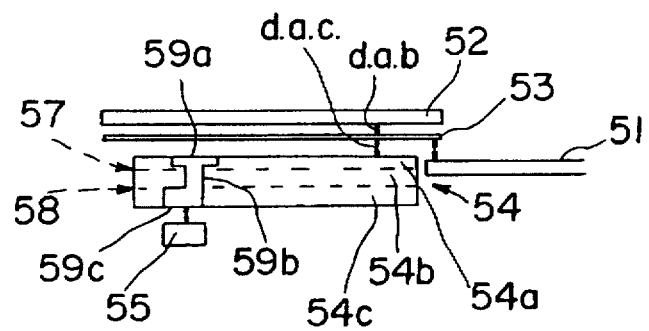
FIG. 6 is a side view of an embodiment of the invention with a brazing ring on the outside of the metal pacemaker can.

Refer now to FIG. 6 in which a piece of cofired ceramic 54 is illustrated in detail. Double arrows a-e indicate where the pieces 52, 53, 51, 54 and 55 get connected. Piece 52 is attached to 54 by melting and wetting the braze alloy 53 between them, then piece 52 is welded to shell 51. Shell 51 is the (in the preferred embodiment titanium) metal can, 53 is a gold brazing alloy in the preferred embodiment, although other brazing alloys may be used, for example copper-silver, gold germanium, gold-tin, or active metal braze, etc. The braze alloy may be applied as a solid piece or as a paste. Block 55 is a capacitor as will be described later. In this simplified example of a multilayer cofired ceramic 54, there are three ceramic layers, 54a, 54b, and 54c. Through each one of these layers, tungsten metal (preferably tungsten, although other metals of similar melting point could be used) is screen printed or written into each layer. Thus, the metal portion 59c shaped as shown would be layered into layer 54c, 59b into 54b and 59a into layer 54a. When these layers are fired together, the dotted line indicators of the separation of layers 57 and 58 will not be visible. The tungsten elements will sinter and by connecting provide a conductive pathway through the cofired ceramic. In preferred embodiments, a gold, nickel or other plating is provided to the upper and lower surfaces of the feedthrough to enhance wire bonding, welding, brazing or otherwise electrically connecting thereto.

Figure 7:
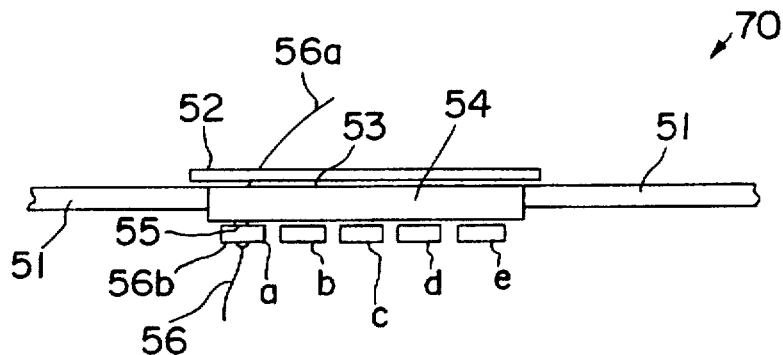
FIG. 7 is a side sectional view of a feedthrough in accord with a preferred embodiment of this invention.

In FIG. 7, a completed assembly is shown. Here, capacitors 55a through 55e are shown connected to the bonding pads which are invisible from this point of view, and wires 56 and 56a are shown wire-bonded to the internal connector pads and the external connector pads, respectively.

Figure 8:
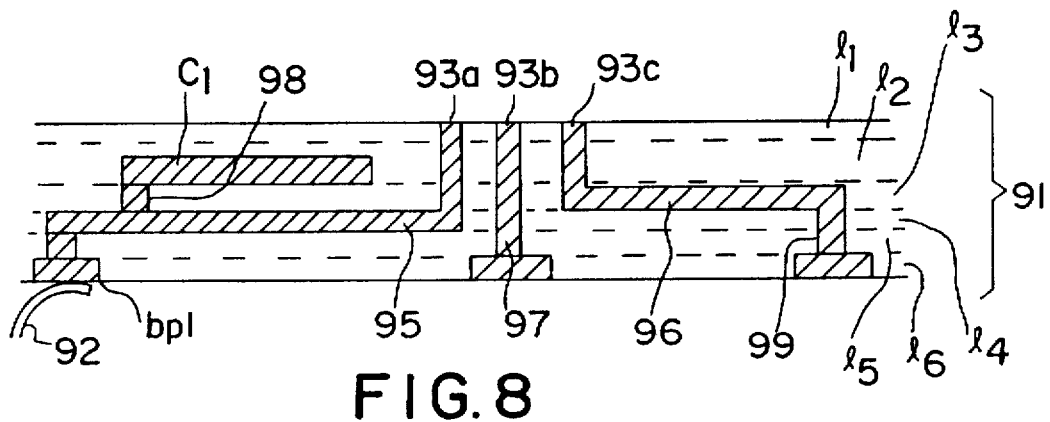
FIG. 8 is a crossection of a multilayered feedthrough design.

FIG. 8 illustrates a section through a six layer feedthrough 91. An internal element e1 is shown connected to both output 93a and input bonding pad 1 and connected thereby to wire 92. Because of the flexibility provided by cofired multilayer ceramics, an element such as e1 could be configured to be a capacitor, a resistor or, an antenna for example. It may need other connections to other points within the circuit going through the multilayered hybrid, but it is not felt necessary to go into further detail on this, for one of ordinary skill in the art would be able to build such elements without additional disclosure. It is known, for instance, that long conductive or resistive strips may be made in a single layer as is illustrated by areas 95 and 96, as well as short blocks which merely connect something, say, element e1 to another layer, element 95. Small elements such as this may form a straight conductor such as conductor 97 making up the bulk of pathway 93b.

Figure 9:
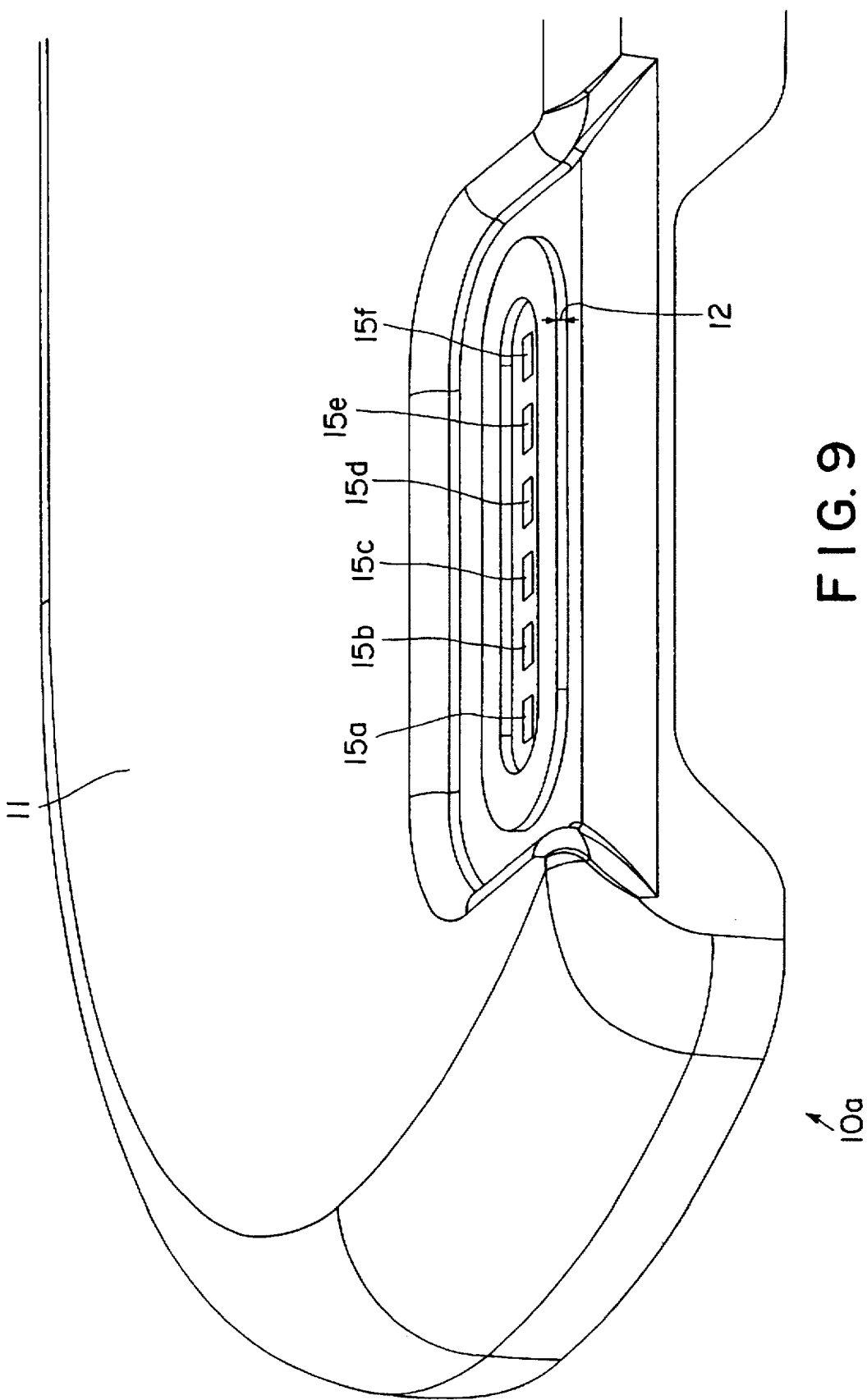
FIG. 9 is an isometric view of an exterior of one part of an implantable device metal can having a preferred embodiment feedthrough mounted therethrough.
Figure 10:
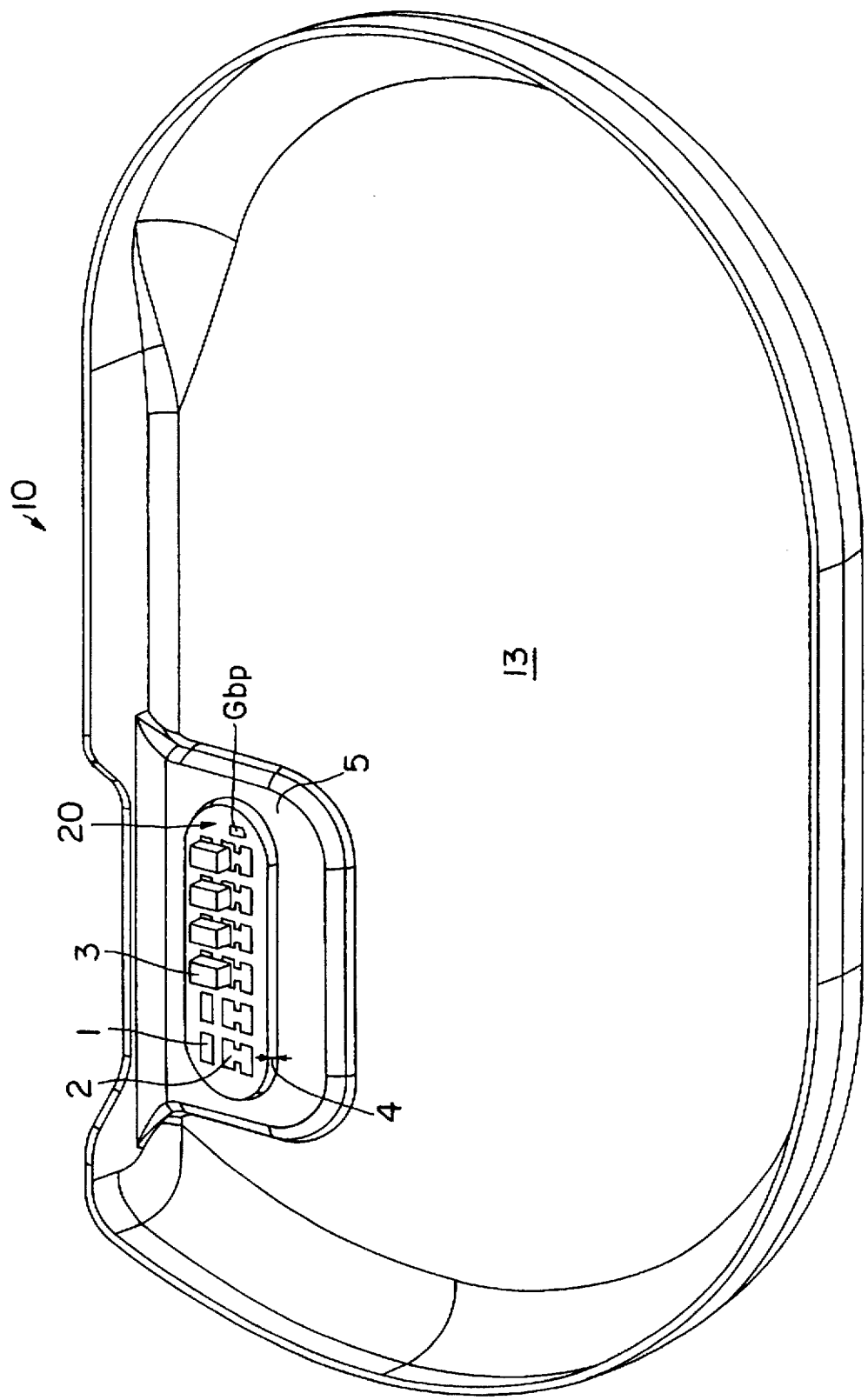
FIG. 10 is an isometric view of the inside of the can of FIG. 9 showing the inside of the mounting area a preferred embodiment feedthrough in accord with this invention.

Before describing FIGS. 9 and 10 in which the shell is illustrated as halves 10 and 10a, several points should be explained further.

The capacitors, illustrated variously with reference to numeral 55, are preferably mounted on the inside of the implantable device. By such mounting there are less long-term reliability problems than might otherwise be, for example were the capacitors to be on the outside of the hermetically sealed enclosure. In the present design, we prefer to braze a weld ring on the side of the ceramic feedthrough that would be on the outside of the implanted device. This provides certain benefits including allowing more room on the inside surface for capacitors and other advantages that will readily become apparent to the user. But it would also be possible to braze the weld ring to the other side of the ceramic if desired. Alternative preferred embodiments include; brazing the ceramic substrate directly into a metal shield eliminating the separate weld ring; and brazing a weld ring directly to the ceramic without a screened tungsten ring on the ceramic by using an active braze alloy.

We presently mount defibrillation diodes on a hybrid substrate inside implantable pulse generators used for cardiac defibrillation. Additional advantage may be had by mounting the diodes on the multilayered feedthrough.

It is expected that implantable devices can be more easily enhanced with multilayer feedthrough conductors since they can accommodate easily six or more feedthroughs for such devices as would accommodate dual chamber bipolar pacing, external antennae and subcutaneous electrodes of various types. The addition of extra leads for sensors outside the can becomes almost a no cost issue.

Figure 11:
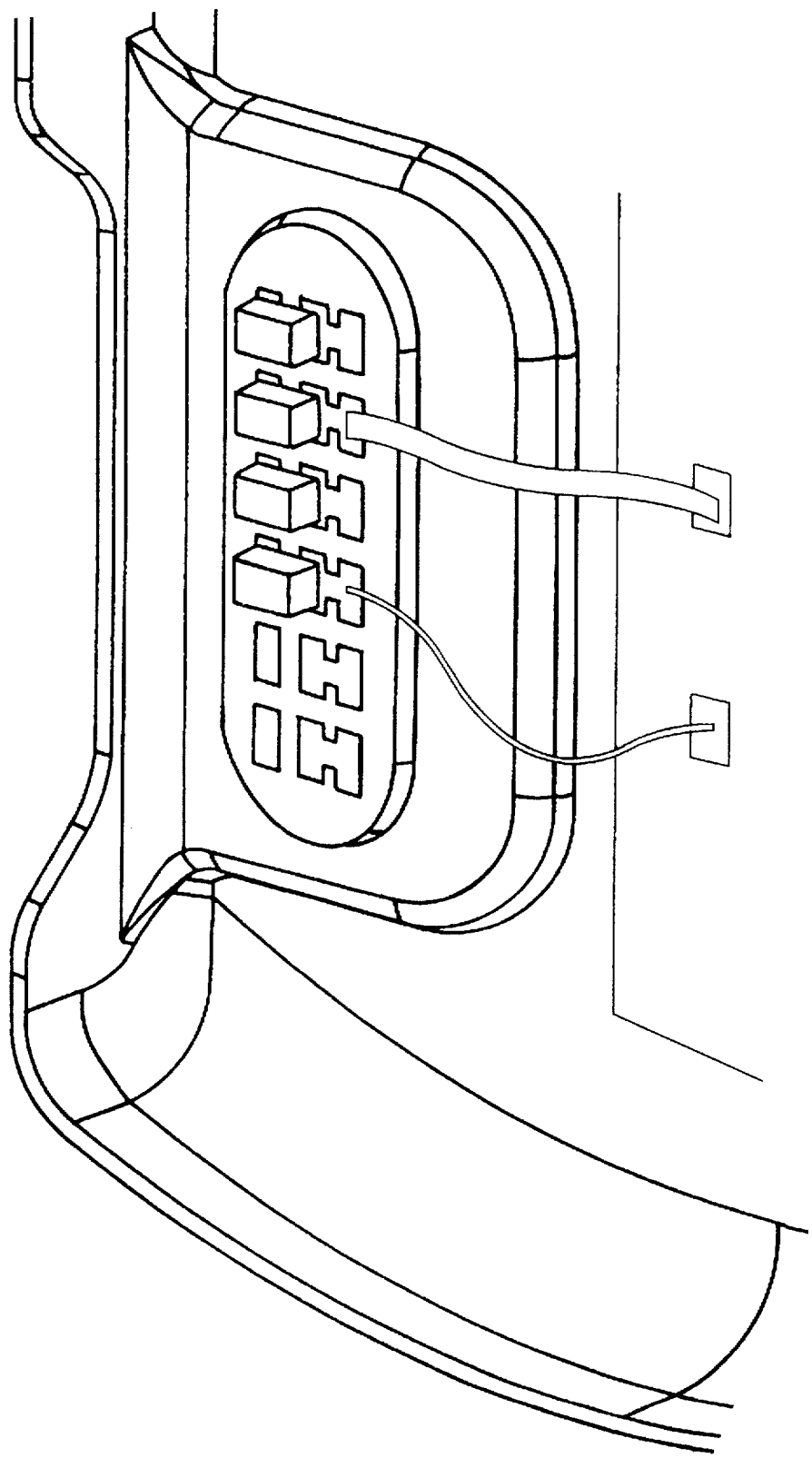
FIG. 11 is an isometric view showing ribbon and wire connections to the invention feedthroughs.

Ribbon conductors may also be used to connect to the connector pads on the ceramic feedthroughs, thereby increasing the possibilities for automated assembly. Especially convenient are the flat, linear arrays available through this invention such automated assembly. See FIG. 11 for detail.

Referring now to FIGS. 9 and 10, opposite sides the same shell halves are illustrated as 10 and 10a. The exterior surface 11 of the shell 10a is shown in FIG. 9 and the interior surface 13 of shell 10 in FIG. 10. In this embodiment, the shell is preferably made of titanium, although other body-safe materials could be used. The interior space of the shells would contain hybrid circuitry and components as well as a large battery for powering its circuitry, although other power sources could also be used if desired. A bonding pad such as pad 2 shown in FIG. 10 connects to an exterior surface bonding pad 15a shown in FIG. 9 through the feedthrough layers illustrated here as 4. The weld ring 12 is fused to the surface 11 of half 10a. A bonding pad such as is illustrated at G could provide for electrical connection from the hybrid "board" in the shell by wire bond or ribbon bond thereto to the outside of the shell through weld ring 12 by a connection through the multilayer feedthrough structure 4. The exterior may have a weld plate on the surface thereof to connect to such a "G" type pad which may be for a ground or "shield jumper". There are internal connections between the capacitor grounds pad 1 and pad G and the weld ring.

In the preferred embodiment these multilayer feedthroughs are ceramic sheet material which, when co-fired, becomes as a single layer. In the FIG. 2 illustration the surface 206 and also on later figures, the individual layers are not visible. This is because once fired, the structure appears to have only one layer. In FIG. 4 for example each layer of this ceramic material (which shows in the illustration as surface 41) may be screened in a pattern with a metal such as tungsten to provide the electrical connections such as are illustrated in FIGS. 8 and 6, for example, that would connect between the inside in FIG. 10 and the outside in FIG. 9.

It should be noted that it is possible that molybdenum or other refractory metal may be used for inter and intra layer conductive pathways in place of tungsten but these are not preferred. Further, if low temperature co-fired technology is used, even gold or other similar metals could be used.

FIGS. 12a and 12b and FIGS. 13 and 14 illustrate applications of this invention by showing connections of the feedthrough taught by the invention to various implantable device embodiments.

Figure 12A:
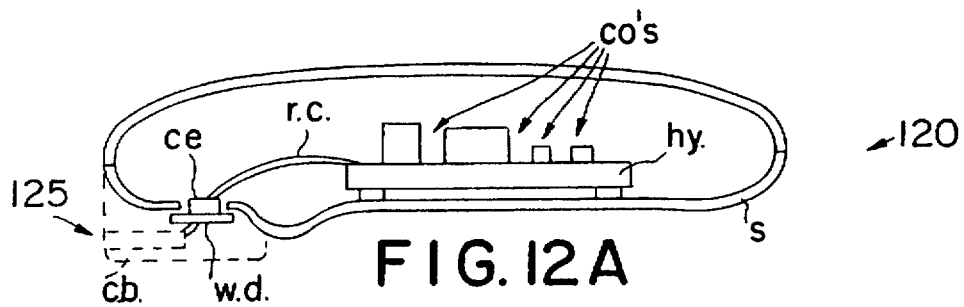
FIGS. 12a and 12b are cutaway side views of different orientations for the inventive feedthrough connection to implanted devices and the circuit elements inside such devices.

In FIG. 12a, a device 120 has a preferably titanium metallic outer shells containing a hybrid circuit board which could be any kind of hybrid circuit board but in preferred embodiment is of the ceramic multilayered described herein. The circuit board is assembled with components and is connected through a ribbon cable rc to the ceramic part of the multilayered feedthrough as described in this invention. By welding a welding ring to the shell the ceramic is firmly affixed to the shell of device 120. A wire bond to the outer surface of the ceramic connector provides for the electrical connection from the opening 125 in the connector block cb through the ceramic multilayered feedthrough, the ribbon cable to the components on the hybrid circuit board hy. The typical use for such a structure would be a pacemaker having a pacing lead inserted into opening 125 in a plastic connector block cb such that pacing and sensing of cardiac activity could be had through the lead by the circuit components on the hybrid within device 120.

Figure 12B:
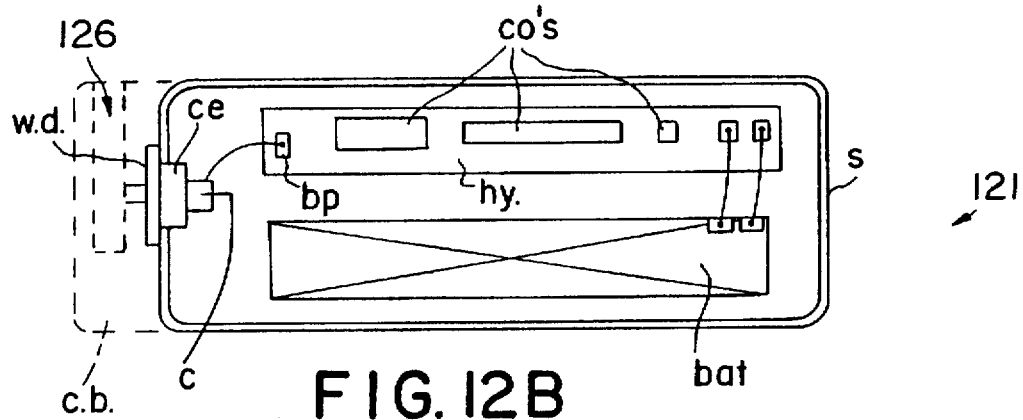
Figure 13:
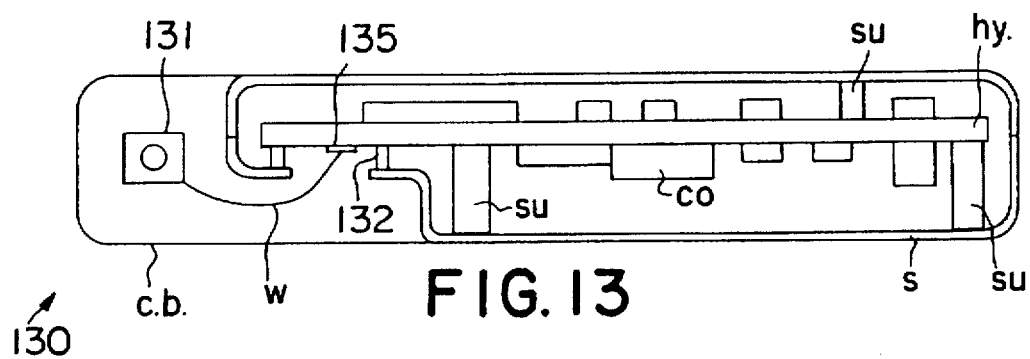
FIG. 13 is another cutaway side view of another embodiment of the invention.
Figure 14:
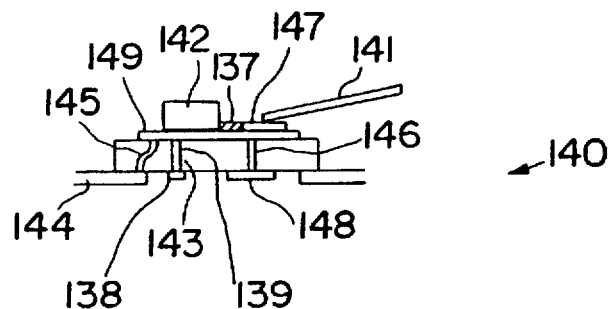
FIG. 14 is an enlarged view of a portion of FIG. 13.

In FIG. 12b, a different orientation for a device using a ceramic feedthrough ce is shown. The device 121 again has a shell s and components co-assembled onto a hybrid circuit board hy. The circuits are powered by a battery bat and at least one bonding pad bp allows for connection between the hybrid circuit board and a connector component mounted to the inside of a ceramic multilayered feedthrough. Again, a welding ring is brazed or welded to the outside of the shell s within an area contained within a plastic connector block cb, and wires bonded to the outside of the multilayered ceramic feedthrough provide for connection which may be inserted into opening 126. FIG. 13 details a device which can be constructed with a slightly different application of the inventive concepts described herein. Device 130 here applies an internal braze ring 132 to one side of the hybrid hy. The hybrid itself is supported by supports su and is also assembled with components co all within a shell s. The difference here is that no separate feedthrough component is used. The hybrid circuit and multilayered feedthrough which provides access to the outside world for the components inside the shell are thus part of one assembly. The connector block is merely fitted over the housing such that a window area is left in the housing for electrical connection to the hybrid circuit board hy as shown. Here a wire bonding pad 135 formed on the exposed surface of the circuit board hy connects a wire w to the lead bore 131 for connecting the lead to the connector block cb of this device 130. One final illustration is had in FIG. 14 in which a ceramic multilayer connector 143 is shown bonded directly to an outer shell 144 and providing connections 145 and 146 therethrough. This illustrates the connection such as 145 for a ground to a shell made of metal 144 to a ground ring 149 which may be within an interior of an implanted device. Again, a connection may be made between an exterior bonding pad 148 and an interior bonding pad 147 or if desired a connection may be made between an exterior bonding pad 138 through feedthrough line 139 to a capacitor 132 the other side of which is connected through a shaded area 137 to an interior bonding pad such as bonding pad 147. It will be understood by those of ordinary skill in the art that the likelihood that only one of the connections will be made between either 139 and 147 or 146 and 147 but probably not both.

Numerous uses and device applications may be found for the inventive concepts herein which are only limited in scope by the following claims.

We claim:

1. A packaging arrangement for the outer packaging of an implantable medical device comprising:
   a ceramic enclosure having an opening for receiving circuitry of said implantable medical device; and
   a multi-layered feedthrough substrate for coupling to said ceramic enclosure at edges around said opening, said substrate having multiple feedthroughs for electrically coupling said circuitry inside said enclosure to the outside of said enclosure.

2. The packaging arrangement in claim 1 further comprising a connector block for coupling to said substrate, and for coupling to at least one electrical lead, said connector block electrically connecting said lead to said feedthroughs.

3. The packaging arrangement in claim 2 further comprising:
   a first weld ring for coupling to said ceramic enclosure;
   a second weld ring for coupling to said first weld ring, and to said multi-layered feedthrough substrate.

4. The packaging arrangement in claim 1 wherein said ceramic enclosure further comprises a metallic outer layer.

5. The packaging arrangement in claim 2 wherein said ceramic enclosure further comprises a metallic outer layer.

6. The packaging arrangement in claim 3 wherein said ceramic enclosure further comprises a metallic outer layer.

7. An implantable package having an inside and an outside, and having a ceramic feedthrough for mounting into said package with an exterior surface and an interior surface such that when assembled the package outside is coextensive with the exterior surface of said feedthrough and the package inside is substantially coextensive with the feedthrough interior surface said package further comprising:
   a ceramic substrate feedthrough co-fired with metal ic conductive interconnects therein at least one of which extends from the exterior surface to said interior surface.

8. A package as set forth in claim 7, such that said package further comprises:
   a metalized electrode grounding ring mounted on the outside of said package electrically connected by a conductive metal pathway through said feedthrough to circuitry inside said package.

9. A package as set forth in claim 8 wherein said metal grounding ring is planar in shape.

10. An implantable medical device having an exterior surface substantially defined by a metal can or shell enclosure with an inside containing circuitry and an outside thereto, said device comprising a ceramic multilayer feedthrough component which component comprises a ceramic substrate feedthrough co-fired with metal interconnects therein at least one of which interconnects provides an electrical pathway that extends from an exterior surface to an interior surface of said feedthrough component, and wherein said device has a welding ring for connecting the feedthrough component to the can in a configuration such that said exterior surface will be substantially coextensive with the outside and said interior surface with the inside of said can or shell, such that circuitry within said can is electrically connected to the outside of said can by said interconnect pathway.

11. An implantable medical device having an exterior surface substantially defined by a metal can or shell enclosure with an inside containing circuitry and an outside thereto, said device comprising a ceramic feedthrough component for providing connection between electrical circuits on an inside of said implantable device to an outside of said implantable device as set forth in claim 10 and further comprising:
on said interior surface of said feedthrough component, a first bonding pad area for holding one side of a surface mount capacitor connected to ground, and having a second bonding area also on said interior surface of said feedthrough component, said second area electrically isolated from said first area except through said surface mount capacitor for holding an opposite side of said surface mount capacitor, said second area also being electrically connected through said ceramic feedthrough to the outside of said implantable medical device.

12. An implantable medical device having an exterior surface substantially defined by a metal can or shell enclosure with an inside containing circuitry and an outside thereto, said device comprising a ceramic feedthrough component for providing connection between electrical circuits on an inside of said implantable device to an outside of said implantable device as set forth in claim 10 and wherein said feedthrough is a ceramic multilayered feedthrough which has encapsulated therewithin a circuit element, from a list of circuit elements: including
resistor, capacitor, antenna, coil, diode, sensor, or inductor.

13. An implantable medical device having an exterior surface substantially defined by a metal can or shell enclosure with an inside containing circuitry and an outside thereto, said device comprising a ceramic feedthrough component for providing connection between electrical circuits on an inside of said implantable device to an outside of said implantable device as set forth in claim 10 and wherein said feedthrough component is a ceramic multilayered feedthrough having at least 2 layers, said feedthrough comprising a pattern of metalization within each of the ceramic layers such that when cofired, said metalization extends from an inner surface to an outer surface of said multilayer feedthrough.

14. An implantable medical device having a feedthrough component as set forth in claim 13 wherein said ceramic feedthrough forms a rigid substrate.

15. An implantable medical device having a feedthrough component as set forth in claim 14 wherein said rigid substrate has an outer surface comprising a linear row of bonding pads.

16. An implantable medical device comprising at least three parts adapted to be hermetically sealed together for implantation into a living body, a connector block part having a lead receptacle formed therein for receiving and electrically connecting to a conductive pathway in a lead body, and having a mounting portion for mounting over a window area of a shell part so as to seal said window from fluids in a body into which said device is to be implanted and wherein an electrical pathway is provided from said electrical connection to said lead to said window within said connector block, a circuitboard part comprising a multilayer ceramic hybrid circuitboard metalization patterned on and through layers therewithin for assembling with electrical components on said circuitboard part and having bonding pads on a surface of said circuitboard part such that at least one of the bonding pads on said circuitboard part is located so as to be exposed to said connector block window for connection to said electrical pathway in said connector block and at least one shell part for housing said circuitboard part and mounting said window of said connector block thereto.

17. A device as set forth in claim 16 wherein said shell comprises two mating parts.

18. An implantable medical device comprising at least three parts adapted to be hermetically sealed together for implantation into a living body, a connector block part having a lead receptacle formed therein for receiving and electrically connecting to a conductive pathway in a lead body, and having a mounting portion for mounting over a window area on an outside surface of a shell part wherein an electrical pathway is provided from said electrical connection from said lead to said window within said connector block, a feedthrough component part for providing electrical connection between the electrical pathway in said window to a bonding pad within an interior surface of said shell part, a circuitboard part comprising a multilayer ceramic hybrid circuitboard metalization patterned on and through layers therewithin for assembling with electrical components on said circuitboard part and having bonding pads on a surface of said circuitboard part such that at least one of the bonding pads on said circuitboard part is located so as to be electrically connected by a flexible wire to said interior bonding pad and at least one shell part for housing said circuitboard part and mounting said window of said connector block thereto.

19. An assembly for an implantable device comprising a package having a feedthrough component as set forth in claim 14 or 18 and wherein said feedthrough is mounted to said package by a connection to a metal coplanar ring mounted to an outer surface of said feedthrough and of said package.

20. An implantable medical device as set forth in claims 9 or 18 wherein said shell part is made of cofired multilayer ceramic.

21. An assembly as set forth in claim 19 wherein said feedthrough component has mounted over it a connector block adapted for connecting at least one lead thereto and wherein a conductive pathway is provided within said connector block to electrically connect at least one of said bonding pads to a conductive pathway in said at least one lead.

* * * * *